United States Patent [19]
Daley et al.

[11] Patent Number: 5,928,649
[45] Date of Patent: Jul. 27, 1999

[54] METHOD OF REVERSING IMMUNOSUPPRESSION IN VACCINES

[75] Inventors: Michael Joseph Daley, Yardley, Pa.; Phillip Wayne Hayes, Warwick, N.Y.

[73] Assignee: American Cyanamid Company, Madison, N.J.

[21] Appl. No.: 08/455,751

[22] Filed: May 31, 1995

Related U.S. Application Data

[63] Continuation of application No. 08/011,888, Feb. 2, 1993, abandoned.

[51] Int. Cl.$^6$ ...................... A61K 39/145; A61K 39/12; A61K 39/02; A61K 39/295
[52] U.S. Cl. ..................... 424/211.1; 424/85.2; 424/85.4; 424/85.6; 424/184.1; 424/278.1; 424/813; 424/815; 424/823; 424/825; 424/197.1; 424/200.1; 424/201.1; 424/202.1; 424/203.1
[58] Field of Search .................. 424/85.2, 85.4, 424/85.6, 184.1, 278.1, 813, 815, 823, 825, 211.1, 197.1, 200.1, 201.1, 202.1, 203.1

[56] References Cited

U.S. PATENT DOCUMENTS

| | | | |
|---|---|---|---|
| 4,185,090 | 1/1980 | McIntire | 424/197.11 |
| 4,557,931 | 12/1985 | Irie et al. . | |
| 4,820,514 | 4/1989 | Cummins | 424/85.4 |
| 4,879,374 | 11/1989 | Cerrette et al. . | |
| 5,108,911 | 4/1992 | Cerrett et al. . | |
| 5,187,087 | 2/1993 | Sondermeijer et al. . | |
| 5,336,488 | 8/1994 | Daley et al. . | |
| 5,342,612 | 8/1994 | Daley et al. . | |
| 5,470,734 | 11/1995 | Sondermeijer et al. . | |
| 5,503,841 | 4/1996 | Doyle et al. . | |

FOREIGN PATENT DOCUMENTS

| | | |
|---|---|---|
| 0537437 A3 | 4/1993 | European Pat. Off. . |
| 0604727 A1 | 7/1994 | European Pat. Off. . |
| 0609739 A1 | 8/1994 | European Pat. Off. . |
| WO88/00971 | 2/1988 | WIPO . |

OTHER PUBLICATIONS

1991 Genzyme Catalog "Cytokine Research Products" pp. 64–65.
Feist et al, FEMS Microbiology Immunology 89: 73–90, 1992.
Reddy et al, Lymphokine Research 9(3):295–307, 1990.
Godson et al, Can.J. Vet. Res., 59:249–255, 1995.
Edelman et al, 33rd Interscience Conf. on Antimicrobial Agents and Chemotherapy. 33/0:153 Abstract#187, 1993.
Edelman et al, 1990, Intern. Rev. Immunol 7:51–66.
Fedorka–Cray et al, 1988 ASM. Mtg. Abstract E–30, p. 114.
Nencioni et al 1987 ASM Mtg Abstract E–51, p. 111.
Anderson et al 1987 ASM Mtg Abstract E–52, p. 111.
Hughes et al, 1992 Vaccine 10/4:226–230.

*Primary Examiner*—Nita Minnifield
*Attorney, Agent, or Firm*—Hamilton, Brook, Smith & Reynolds, P.C.

[57] ABSTRACT

A method of reversing or preventing immunosuppression or antigenic interference associated with combination vaccines in mammals, is disclosed. Cytokines, or cytokine inducer, are administered in conjunction with the combination vaccine. The cytokine or cytokine inducer can be administered concurrently with or subsequently to the vaccine, and can be recombinantly produced or isolated from cell culture.

20 Claims, 2 Drawing Sheets

METHOD OF REVERSING IMMUNOSUPPRESSION IN VACCINES

This is a continuation of application(s) Ser. No. 08/011,888 filed on Feb. 2, 1993 now abandoned.

BACKGROUND

Bovine respiratory disease is estimated to result in annual losses to the North American cattle industry in excess of 600 million dollars. *Pasteurella haemolytica* is recognized as the most important etiological agent in the bovine respiratory disease complex. However, other organisms such as bovine viral diarrhea virus (BVD) and bovine respiratory syncytial virus (BRSV) have been identified as pathogens which may play a significant role in the respiratory disease complex in feedlot cattle. Martin et al. (*Can. J. Vet. Res.* 53:355 (1989)) reported that seroconversion to *P. haemolytica* cytotoxin, RSV and BVD were predictive of respiratory disease cases, explaining approximately 69% of all respiratory disease cases in the feedlots.

Vaccines have been generated against many bovine respiratory diseases; however, industry demand to combine several vaccines within a single delivery system has caused increasing concern with the problem of interference and virally induced immunosuppression. The immunosuppressive nature of some antigenic epitopes or antigenic competition may render components of a "protective" vaccine useless or deleterious (Ishikura, H. et al. (1988) *Immunol. Rev.* 106:93; Mueller, D. H. et al. (1989) *Annu. Rev. Immunol.* 7:445; Scott, P. et al. (1989) *Immunol. Rev.* 112:161; Stephens, L. R. (1990) *Can. J. Vet. Res.* 54:541–544; AralaChaves, M. P. et al. (1988) *Am. J. Vet. Res.* 49:1955). This immunosuppression is often heterogeneous in outbred species, and is difficult to predict. A method of reducing or eliminating this antigenic interference would be useful in facilitating vaccination through combination vaccines, as well as minimizing morbidity and mortality due to the immunosuppressive effect of a vaccine.

SUMMARY OF THE INVENTION

The current invention relates to the administration of a cytokine in conjunction with a vaccine. As described herein, it has been discovered that administration of a cytokine in conjunction with a vaccine reverses the viral-induced immunosuppression or antigenic interference of the vaccine in a mammal, and renders effective vaccines which would otherwise lack sufficient potency and immunogenicity. As such, the present invention relates to a method for reversing viral-induced immunosuppression of a vaccine when the vaccine is administered to a mammal.

In one embodiment of the current invention, administration to cattle of the cytokine bovine recombinant interleukin-1β (R-BoIL-1β) in conjunction with a combination vaccine reverses viral-induced immunosuppression in the combination vaccine. After vaccination of cattle with a combination vaccine containing killed bovine herpes virus-1 (BHV-1), bovine viral diarrhea virus (BVD), parainfluenza type 3 (PI-3), and *Pasteurella haemolytica* toxoid extract, challenge with *P. haemolytica* reveals that those animals administered the combination vaccine and r-BoIL-1β tend to have higher titers to BVD, BHV-1 and PI-3, as compared to vaccinated animals not administered the cytokine. In addition, animals administered the combination vaccine alone tend to have more clinical signs, including increased temperature or respiratory distress, and demonstrate more disease pathology than either the animals administered both the vaccine and r-BoIL-1β, or the non-vaccinated controls. In a second embodiment, administration to pigs of the bovine cytokine r-BoIL-1β in conjunction with a previously ineffective vaccine renders the vaccine effective. After vaccination of pigs with a vaccine containing *Streptococcus suis* (*S. suis*) serotypes 1 and 2, challenge with *S. suis* reveals that those animals administered the vaccine and r-BoIL-1β or r-BoIL-2 in large doses generally have fewer clinical signs of *S. suis* infection and lower mortality than those administered the vaccine alone.

These results demonstrate that administration of a cytokine concurrently with a vaccine eliminates immunosuppression and antigenic interference, and also renders an ineffective vaccine effective.

Administration of a cytokine, or a cytokine inducer, can thus be used to reduce, reverse or prevent both locally and systemically manifested immunosuppression or antigenic interference related to administration of a vaccine in a mammal, as well as render effective vaccines otherwise insufficiently potent or immunogenic. The cytokine or cytokine inducer can be administered concurrently with the vaccine, or either before or after administration of the vaccine. Both recombinantly produced cytokines or cytokine inducers, and cytokines or cytokine inducers derived from animal cells or other sources, are useful in the present invention. Use of cytokines or cytokine inducers are thus helpful in the administration of a variety of vaccine compositions, including those comprised of bacterins, toxoids, and/or inactivated virus particles. The vaccine components can be agents isolated from infected cells, or recombinant or synthesized agents.

DETAILED DESCRIPTION OF INVENTION

Figure 1:
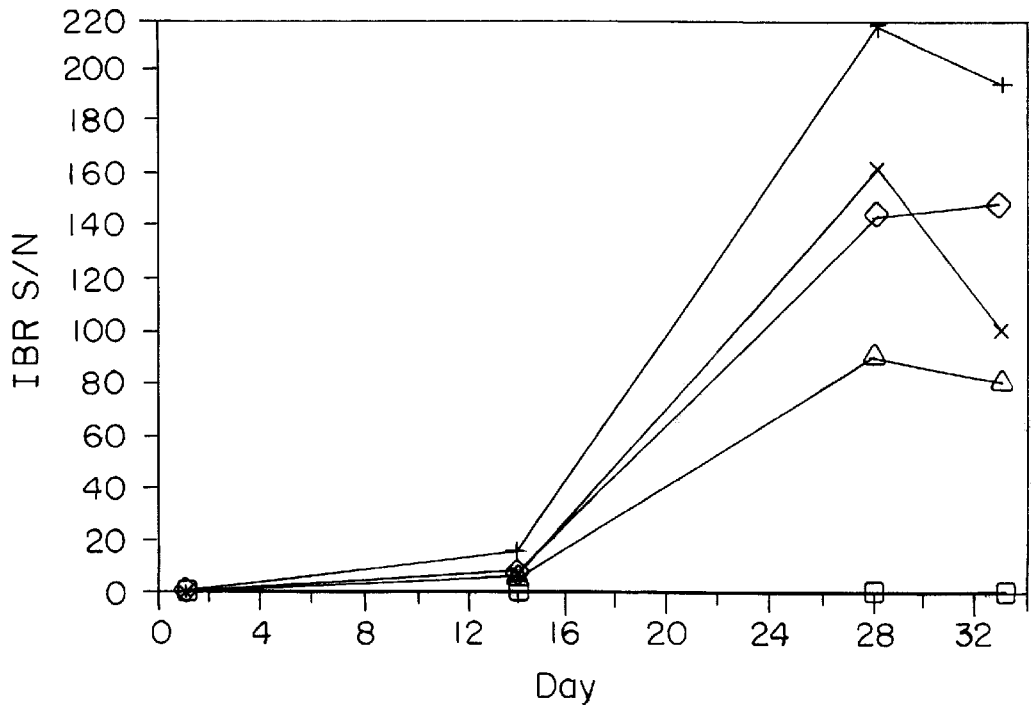
FIG. 1 is a graphic representation of the measure of serum neutralization antibody titers to BHV-1 at various times after immunization with a combination vaccine containing four viral components and *Pasteurella haemolytica* toxoid (PV-5). Each point represents the mean of duplicate determinations: control group (open squares); PV-5 combination viral vaccine (open triangles); PV-5 combination viral vaccine+ r-BoIL-1β (X); PV-5 combination vaccine with *P. haemolytica* toxoid diluted 1:5 plus r-BoIL-1β (+); and PV-5 combination vaccine with *P. haemolytica* diluted 1:25 (open diamonds).

The present invention relates to a method of reducing, reversing, or eliminating immunosuppression or antigenic interference associated with vaccines administered to a mammal. Single or multiple combinations of vaccines are often unpredictably immunosuppressive in various animals; these immunosuppressive effects render the vaccine useless or potentially harmful to the vaccinated individuals. It is believed that competing antigenic determinants or suppressive epitopes of antigens in a combination vaccine contribute to this phenomenon. Applicants have discovered that administration of cytokines or cytokine inducers in conjunction with a vaccine can be used to remedy both local and systemic immunosuppressive effects of the antigens. Cytokines or cytokine inducers can be used to eliminate immunosuppression or antigenic interference of a single immunosuppressive antigen in a vaccine, of a single immunosuppressive antigen in a combination vaccine (a vaccine containing more than one antigen or component), or of several immunosuppressive antigens in a combination vaccine. The invention is useful for both inbred and outbred mammals, including human beings, and can be used safely in individuals which are immunocompromised from stress, surgical procedures, parturition and/or disease states.

In this manner, cytokines are used to improve the efficacy of existing live or killed vaccines, or enable creation of new vaccines from antigens which require combination with cytokines to achieve suitable potency and immunogenicity, and to eliminate deleterious effects on other components of the vaccine. Moreover, it is now possible to safely administer a larger combination of antigens to animals, to provide a better and protective biological response. The invention also facilitates safe and effective combination of several antigens to provide improved immunizing protection against single or multiple pathogens.

The vaccines of this invention are those currently available or newly derived compositions, and comprise a number of biological substances, particularly antigens such as, but not limited to bacterins, toxoids, inactivated virus particles, modified live viral particles, or other immunogenic components of pathogens. These vaccine components may be recombinantly produced, synthesized, or isolated from an infected host cell. If recombinant vaccine components are used, the cytokine or cytokine inducer can be molecularly coupled to the recombinant component of the vaccine by crosslinking with glutaraldehyde or disulfide bridging, and introduced as a single product.

Preferred cytokines used in the current invention are interleukins, such as IL-1, IL-2, IL-4, IL-5, IL-6, IL-7 or IL-10; interferons, including $\alpha$-, $\beta$- or $\gamma$-interferon; or colony stimulating factors, such as macrophage colony stimulating factor, granulocyte colony stimulating factor or granulocyte macrophage stimulating factor. Alternatively, a cytokine inducer, such as endotoxin, is also useful to promote generation of endogenous cytokines within the mammal. Such cytokine inducers can be chemicals, plant components (i.e., lectins, toxins, etc.), or other components. The term "cytokine inducer", as used herein, includes agents which elicit endogenous release or production of a cytokine.

Furthermore, a cytokine in combination with a cytokine inducer is useful in the present method as well. The cytokine or cytokine inducer used in the current method can be isolated from cultured plant or animal cells, including human cells. Alternatively, the cytokine or cytokine inducer can be generated by recombinant methods.

The cytokine or cytokine inducer is administered concurrently with the vaccine, or it is administered prior or subsequent to the administration of the vaccine, preferably within 96 hours before or after the vaccine. The cytokine or cytokine inducer is administered in a therapeutically effective amount, which is the amount sufficient to counteract the immunosuppressive effects or the antigenic interference associated with the combination vaccine. The cytokine or cytokine inducer is administered intravenously, intramuscularly, orally, rectally or subcutaneously, and can be combined with pharmaceutically acceptable carriers, adjuvants and vehicles. The cytokine or cytokine inducer can be administered in the same manner and at the same site as the vaccine, or can be administered at a different site or in a different manner.

In one embodiment of the current invention, the cytokine bovine recombinant interleukin-1$\beta$ (r-BoIL-1$\beta$) is used to prevent the immunosuppressive effects of a combination vaccine administered to cattle. As further described in Example 1, r-BoIL-1$\beta$ is administered to calves in conjunction with a combination vaccine (Langford Laboratories, Inc., Kansas City, Mo.) containing bovine herpes virus-1 (BHV-1), bovine viral diarrhea virus (BVD), parainfluenza type 3 (PI-3), and *Pasteurella haemolytica* toxoid extract. Control groups of calves receive either physiologic saline, or combination vaccine without r-BoIL-1$\beta$B. Calves are vaccinated twice and then challenged with *P. haemolytica*. Those calves which are administered the combination vaccine in conjunction with r-BoIL-1$\beta$ tend to have higher titers to BVD, BHV-1 and PI-3, as compared to vaccinates alone. In addition, animals administered the combination vaccine in conjunction with r-BoIL-1$\beta$ demonstrate good protection against *P. haemolytica* challenge compared to the non-vaccinates, whereas those animals administered the combination vaccine alone tend to have more clinical signs and lung consolidation than either the animals administered both the vaccine and r-BoIL-1$\beta$, or the non-vaccinated controls. These results demonstrate that the protective effects of a vaccine to *P. haemolytica* toxoid are neutralized when combined with viral vaccines: the vaccinates of this combined vaccine perform worse than the non-vaccinates. In contrast, the vaccine with the same viral components and *P. haemolytica* toxoid provide good protection when the cytokine r-BoIL-1$\beta$ is added to the vaccine. The protective effects are eliminated as the toxoid antigen is diluted while keeping the viral components and r-BoIL-1$\beta$ levels constant. Although a loss of the protective effects to challenge is observed, no enhanced susceptibility as with the combination vaccine alone is noted. This suggests that the enhanced susceptibility is due to non-specific viral-induced immunosuppression by the viral components, as well as specific immunosuppression of the response to *P. haemolytica* toxoid. An examination of injection site muscle tissue following vaccination reveals no identifiable changes in the tissue.

In a second embodiment of the current invention, the cytokine bovine recombinant interleukin-1$\beta$ (r-BoIL-1$\beta$) or bovine recombinant interleukin-2 (r-BoIL-2) is used to render effective a vaccine administered to pigs. As further described in Example 2, r-BoIL-1$\beta$ or r-BoIL-2 is administered to pigs in conjunction with a commercial *S. suis* vaccine (Oxford Laboratories, Type 1 and 2). Control groups of pigs receive either no vaccine, or vaccine without r-BoIL-1$\beta$ or r-BoIL-2. Pigs are subsequently challenged with *S. suis*. Animals administered the vaccine in conjunction with high doses of r-BoIL-1$\beta$ or r-BoIL-2 demonstrate good protection against challenge compared to the non-vaccinates, whereas those administered the vaccine alone tend to have more clinical signs and mortality than either the non-vaccinates or those administered the vaccine in conjunction with r-BoIL-1$\beta$ or r-BoIL-2.

The invention is further illustrated by the following Examples.

EXAMPLE 1

Administration of a Cytokine in Conjunction with a Combination Vaccine in Cattle A. Materials and Methods Vaccines The combination vaccine is a combination of *Pasteurella haemolytica* toxoid extract (PRESPONSE™, Langford Laboratories, Inc.), inactivated IBR, PI3, BVD, BRSV, adjuvanted with MUNOKYNIN™ (Langford Labs). The vaccine for some groups is mixed with 15 µg per dose recombinant bovine interleukin-1. This dose is based upon previous data which established an optimal immunopotentiating dose of approximately 100 ng/kg of body weight. The dilutions (1:5 and 1:25) are made of the *Pasteurella haemolytica* bacterial extract only. The viral, adjuvant and r-BoIL-1β components of all vaccines remain constant.

Animals and Experimental Design

Forty Holstein calves, 2–6 months of age, are randomized into five groups of eight. The five groups are: 1) control, injected intramuscularly with physiologic sterile saline; 2) combination vaccine; 3) combination vaccine+15 µg r-BoIL-1β; 4) combination vaccine with PRESPONSE™ diluted 1:5+µg r-BoIL-1β; and 5) combination vaccine with PRESPONSE™ diluted 1:25+µg r-BoIL-1β. All calves are vaccinated on day 0 and 21 of the experiment with the respective vaccines on day −7, 0, 7, 14, 21, 35, 42 and 48. All calves are bled for serum titers to various components of the vaccines. All calves are challenged with *Pasteurella haemolytica* on day 42 and autopsied 6 days later. Serum neutralizing antibody titers to BHV-1 and nasal excretion of the virus are monitored at various periods during the experiment. Clinical signs are monitored daily throughout the duration of the experiment for rectal temperature and any respiratory distress.

B. Effects of Cytokine Administration on Immunogenicity

Antibody and Serum Neutralizing Titers

Figure 2:
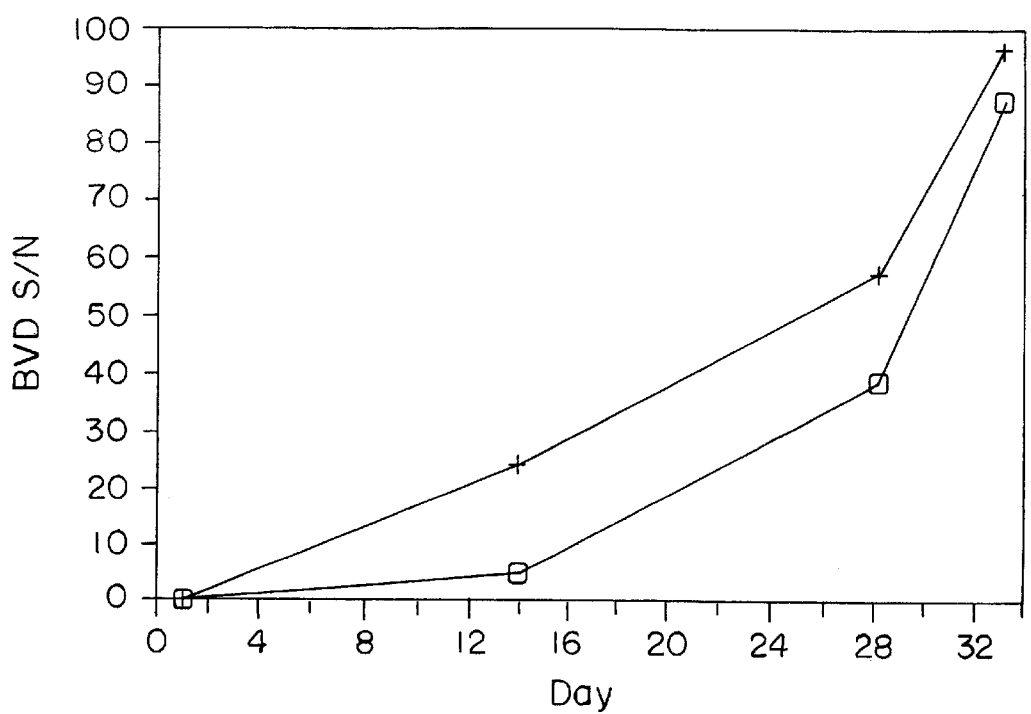
FIG. 2 is a graphic representation of the measure of serum neutralization antibody titers to bovine viral diarrhea virus (BVD) at various times after immunization with PV-5. Each point represents the mean of duplicate determinations: PV-5 combination viral vaccine (open squares), or PV-5 combination viral vaccine plus r-BoIL-1β (+).
Figure 3:
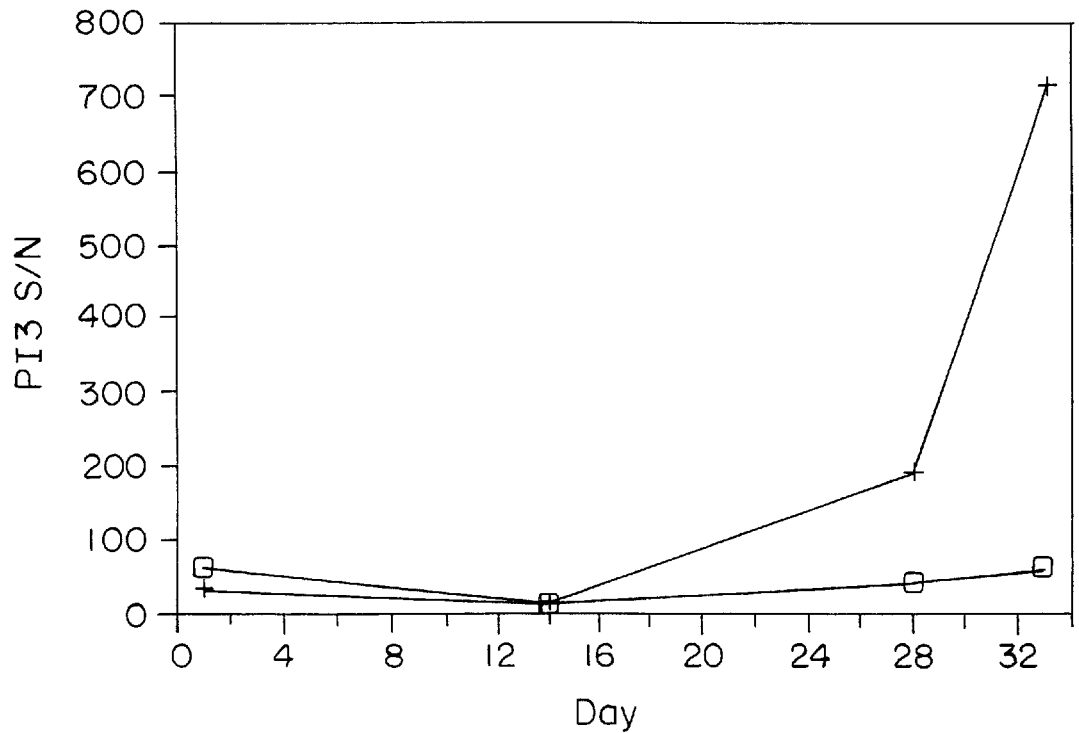
FIG. 3 is a graphic representation of the measure of serum neutralization antibody titers to parainfluenza type 3 virus (PI-3) at various times after immunization with PV-5. Each point represents the mean of duplicate determinations: PV-5 combination viral vaccine (open squares), or PV-5 combination viral vaccine plus r-BoIL-1β (+).

There is a tendency for animals administered r-BoIL-1β to have higher serum neutralizing titers to BHV-1 as shown in FIG. 1. However, because of the small sample size and the variation in titers these differences are not statistically significant. Similarly, serum neutralizing titers to BVD and PI-3 are higher in the r-BoIL-β treated animals as shown in FIGS. 2 and 3. Again, these differences are not statistically significant given the small number of animals and the variation in the titers observed. High pre-titers to both *Pasteurella haemolytica* and BRSV preclude the ability to observe induction of specific titers to *Pasteurella haemolytica* or BRSV.

Figure 4:
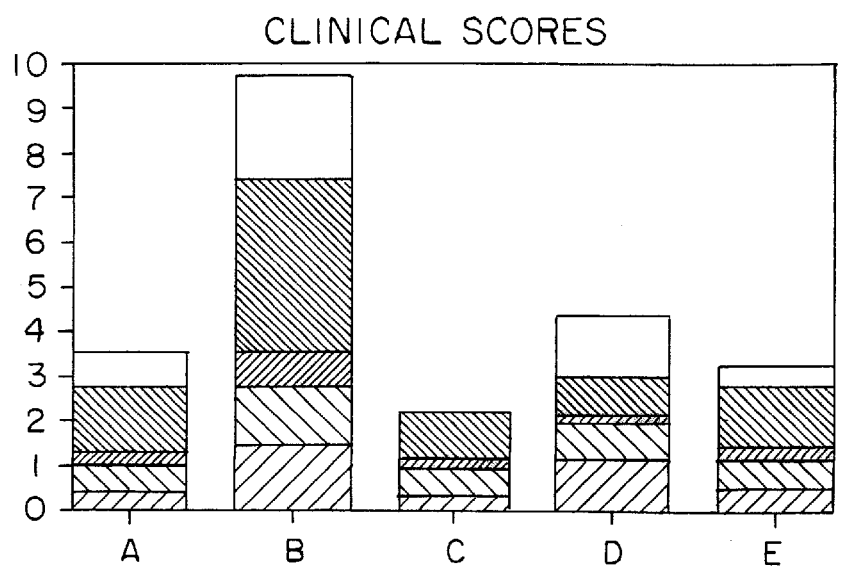
FIG. 4 is a graphic representation of the summation of clinical scores after *P. haemolytica* challenge. Each bar represents the summation of clinical scores for days of increased temperature (▨) or respiratory distress (▧) mean daily (▨) and five-day summation (▧) of clinical scores after challenge; and lung lesions at necropsy (■) Each of the following groups are represented: control (A); PV-5 combination viral vaccine (B); PV-5 combination viral vaccine plus r-BoIL-1β (C); PV-5 combination viral vaccine with *P. haemolytica* toxoid diluted 1:5 plus r-BoIL-1β (D); PV-5 combination viral vaccine with *P. haemolytica* toxoid diluted 1:25 plus r-BoIL-1β (E).

Clinical Signs and Necropsy Findings After Challenge with Pasteurella haemolytica The non-vaccinates demonstrate moderate clinical signs and lung lesions at necropsy as shown in FIG. 4. Surprisingly, those administered the combination vaccine which contain the protective *Pasteurella haemolytica* toxoid (PRESPONSE™) tend to have more severe clinical signs and 2–3 times more lung lesions. However, addition of r-BoIL-1β to the combination vaccine significantly improves the clinical response to challenge and totally prevents any lung lesions after challenge. Furthermore, the protective nature of the vaccine is eliminated when the PRESPONSE™ component is eliminated from the vaccine. Both the diluted PRESPONSE™ groups behave approximately equivalent to the non-vaccinates, as shown in FIG. 4. An examination of the bovine muscle tissue three weeks after injection of PRESPONSE™ with or without interleukin revealed no identifiable changes in the muscle attributable to the injections.

EXAMPLE 2

Administration of a Cytokine in Conjunction with a Vaccine in Pigs

A. Animals and Experimental Design

Sixty, 4-week old pigs from a herd with no known history of *S. suis* are used. Eight pigs (except Group 1) are allotted by weight and gender to one of the following eight groups: Group 1: nonvaccinated controls (4 pigs); Group 2: vaccinated controls; Group 3: vaccinated+r-BoIL-1β at 100 ng/kg; Group 4: vaccinated+r-BoIL-1β at 1,000 ng/kg; Group 5: vaccinated+r-BoIL-1β at 10,000 ng/kg; Group 6: vaccinated+r-BoIL-2β at 2.5 µg/kg; Group 7: vaccinated+r-BoIL-2β at 25 µg/kg; Group 8: vaccinated+r-BoIL-2β at 250 µg/kg. At the start of the experiment (day 0), pigs are vaccinated intramuscularly with a commercial *S. suis* vaccine (Oxford Laboratories, types 1 and 2). At vaccination, pigs are injected intramuscularly with their respective cytokine treatment. Pigs receive additional cytokine injections for two consecutive days. On day 21, all pigs are injected intravenously with $3.5 \times 10^5$ colony forming units of a log phase culture of *S. suis* type 2. Pigs are weighed weekly and body weights recorded. Pigs are observed daily following challenge (early morning) and the following clinical signs are recorded: dyspnea, nasal discharge, depression, lameness, and CNS disorders. Rectal temperatures are recorded daily from days 21 through 28. All pigs are euthanized by electrocution on day 28 and gross lesions, including meningitis, pleuritis, pericarditis, peritonitis, synovitis, and pneumonia (lung weight/body weight) are scored and recorded.

B. Effects of Cytokine Administration on Immunogenicity

Depending on the dosage used, in vivo use of r-BoIL-1β and r-BoIL-2 causes dramatic effects on the physiology and immunology of 4-week-old pigs. Peripheral blood mononuclear cells (PBMC), positive for CD8, are increased in pigs treated with the high dose of r-BoIL-1β and in pigs treated with r-Boil-2 at 25 µg/kg when compared with values from control pigs (data not shown). Pigs injected with r-BoIL-1β at 10,000 ng/kg display clinical signs in response to the cytokine treatment. Continued injections of 10,000 ng/kg r-BoIL-1β cause some pigs to display CNS disturbances (paddling). The adverse effect of the highest dose of r-BoIL-1β is reflected in the poor growth performance in these pigs during the first two weeks of the study (Table 1). However, even though these pigs are effected by the r-BoIL-1β injections, they respond best to the *S. suis* challenge. Their enhanced resistance to *S. suis* is perhaps best shown by their positive average daily gain during the week of infection when pigs in all other treatment groups are losing weight.

TABLE 1

Average daily gain (kg) of pigs vaccinated and challenged with *S. suis* and administered rBoIL-1β or rBoIL-2 as adjuvants at vaccination.

| | TREATMENT | | | | | | | |
|---|---|---|---|---|---|---|---|---|
| | | rBoIL-1β (ng/kg) | | | rBoIL-2 (μg/kg) | | | |
| Period (day) | Control | 100 | 1,000 | 10,000 | 2.5 | 25 | 2.50 | SE | Prob. |
| 0–7 | .29$^a$ | .27$^a$ | .31$^a$ | .12$^b$ | .29$^a$ | .23$^a$ | .26$^a$ | .03 | .001 |
| 0–14 | .38$^{ab}$ | .35$^a$ | .38$^a$ | .30$^b$ | .38$^a$ | .31$^{ab}$ | .36$^{ab}$ | .03 | .06 |
| 0–21 | .42$^{ab}$ | .41$^{ab}$ | .44$^a$ | .36$^{ab}$ | .43$^{ab}$ | .35$^b$ | .39$^{ab}$ | .03 | .05 |
| 21–28 | .15$^a$ | .08$^{ab}$ | .04$^{ab}$ | .13$^b$ | .02$^{ab}$ | .14$^a$ | .07$^a$ | .11 | .07 |
| 0–28 | .30$^{ab}$ | .30$^{ab}$ | .33$^a$ | .30$^{ab}$ | .31$^{ab}$ | .23$^b$ | .26$^{ab}$ | .03 | .03 |

Pigs were vaccinated on day 0 and administered cytokines on days 0, 1, and 2. All pigs were challenged with *S. suis* 21 days (day 21) after vaccination. Values are least squares means, n = 8.
$^{ab}$Means within rows not sharing common superscripts differ.

Similar to the growth performance data, Table 2 shows data that indicates that pigs treated with the highest dose of r-BoIL-1β are least effected by the challenge with *S. suis*. The day after challenge with *S. suis*, pigs in all treatment groups show similar clinical signs of disease. However, on day 2 postchallenge, pigs treated with r-BoIL-1β at 10,000 ng/kg are less effected clinically by the *S. suis* challenge when compared to values from control pigs, and from pigs that received the vaccine without a cytokine. The trend for pigs from the highest dose r-BoIL-1β treatment group to have lower clinical signs of disease continues throughout the experiment. Furthermore, since 3 out of 8 control pigs died by day 3, the lack of difference in morbidity and mortality between the non-vaccinated control pigs and the vaccinate controls indicates that there is no treatment effect of vaccination alone.

Pigs treated with the highest dose of r-BoIL-1β do not die when challenged with *S. suis* (Table 3). Pathological lesions caused by *S. suis* are lowest in pigs that received r-BoIL-1β as a vaccine adjuvant when compared to values from control pigs (Table 3).

TABLE 2

Pooled clinical signs of pigs vaccinated and challenged with *S. suis* and administered rBoIL-1β or rBoIL-2 as adjuvants at vaccination.

| | | | TREATMENT | | | | | | |
|---|---|---|---|---|---|---|---|---|---|
| | | | | rBoIL-1β (ng/kg) | | | rBoIL-2 (μg/kg) | | |
| Day | Nonvaccinates | Control | 100 | 1,000 | 10,000 | 2.5 | 25 | 250 | SE |
| 0 | 0.0 | 0.0 | 0.0 | 0.0 | 0.0 | 0.0 | 0.0 | 0.0 | 0.0 |
| 1 | 8.0 | 7.3 | 9.3 | 8.1 | 7.5 | 7.4 | 9.9 | 7.5 | .9 |
| 2 | 7.0 | 8.3$^b$ | 5.7$^{ab}$ | 7.3$^{ab}$ | 5.1$^b$ | 7.6$^{ab}$ | 7.5$^{ab}$ | 7.4$^{ab}$ | 1.1 |
| 3 | 5.5 | 6.2$^{ab}$ | 5.9$^{ab}$ | 5.3$^{ab}$ | 3.1$^b$ | 5.3$^{ab}$ | 8.7$^b$ | 6.5$^{ab}$ | 1.2 |
| 4 | 6.3 | 6.2$^{ab}$ | 4.4$^{ab}$ | 3.4$^{ab}$ | 2.8$^a$ | 4.8$^{ab}$ | 7.2$^b$ | 5.0$^{ab}$ | 1.2 |
| 5 | 6.3 | 2.8 | 4.3 | 3.6 | 1.3 | 3.5 | 4.8 | 1.8 | 1.3 |
| 6 | 3.0 | 2.0$^{ab}$ | 3.0$^{ab}$ | 2.4$^{ab}$ | 1.4$^a$ | 1.8$^{ab}$ | 4.7$^b$ | 1.2$^{ab}$ | 1.1 |
| 7 | 2.0 | 2.0 | 1.7 | 3.4 | 1.8 | 1.0 | 3.2 | .83 | .9 |

All pigs were challenged with *S. suis* 21 days (day 0) after vaccination. Scoring = 0 to 3 (normal to severe) for dyspnea, nasal discharge, depression and CNS disorders; 0 to 4 (normal to down) for lameness; and 0 to 5 (normal to >107° F.) for rectal temperature. Values are least squares means. $^{ab}$Means within rows not sharing common superscripts differ (P < .05).

TABLE 3

Mortality and necropsy findings of pigs vaccinated and challenged with S. suis and administered rBoIL-1β or rBoIL-2 as adjuvants at vaccination.

| | | TREATMENT | | | | | | | |
|---|---|---|---|---|---|---|---|---|---|
| | | | rBoIL-1β (ng/kg) | | | rBoIL-2 (μg/kg) | | | |
| Item | Nonvaccinates | Control | 100 | 1,000 | 10,000 | 2.5 | 25 | 250 | SE |
| Mortality (%) | 25.0 | 37.5 | 25.0 | 37.5 | 0.0 | 25.0 | 25.0 | 25.0 | — |
| Necropsy Score | 7.55 | 7.88[a] | 5.14[b] | 5.12[b] | 5.00[b] | 6.14[a] | 7.14[a] | 7.00[a] | .92 |
| Lung Weight/ Body Weight (%) | 1.59 | 1.65 | 1.57 | 1.72 | 1.27 | 1.46 | 1.42 | 1.48 | .16 |

All pigs were challenged 21 days after vaccination with S. suis and necropsied at death or 7 days after challenge. Necropsy scoring = 0 to 2 (normal to severe) for pleuritis, pericarditis, meningitis, and peritonitis and 0 to 4 (normal to severe) for synovitis. Values are least squares means. [a,b]Means within rows not sharing common superscripts differ ($P < .05$). [a]Control vs. 10,000 ng/kg rBoIL-1β, $P = .10$.

Natural killer cell cytotoxicity is increased in pigs treated with the high dose of r-BoIL-2. Interestingly, there are no treatment differences in cytotoxic responses on day 7, but at the end of the study, pigs injected with r-BoIL-2 at 250 μg/kg have greater cytotoxic activity against K562 target cells when compared to all other treatment groups. Pigs that receive a single injection of the vaccine have similar antibody responses to S. suis as nonvaccinated animals. Vaccination against S. suis with a vaccine adjuvanted with bovine cytokines, in all cases, yields numerically higher antibody responses when compared to values from control pigs. The highest antibody response to the S. suis vaccine is found in the pigs that are treated with r-BoIL-1β at 10,000 ng/kg.

These data clearly show that r-BoIL-1β (10,000 ng/kg), administered intramuscularly for three consecutive days at vaccination, is more effective than only the S. suis vaccine in protecting pigs against a S. suis challenge. Pigs treated with the highest dose of r-BoIL-1β have less severe clinical signs of the disease after challenge, better growth performance during the infection, less severe pathological lesions caused by the bacteria, and no pigs on this treatment group died from the bacterial challenge. A dose between 1,000 ng/kg to 10,000 ng/kg is the preferred embodiment.

Those skilled in the art will recognize, or be able to ascertain using no more than routine experimentation, many equivalents to the specific embodiments of the invention described specifically herein. Such equivalents are intended to be encompassed in the scope of the following claims.

The invention claimed is:

1. A method of reducing or inhibiting antigenic interference associated with a vaccine comprising antigens from more than one pathogen in a mammal, said method comprising: administering in conjunction with the vaccine an IL-1 or an IL-1 inducer or a combination thereof in a pharmaceutically acceptable vehicle.

2. The method of claim 1, wherein the IL-1 or IL-1 inducer is administered concurrently with the vaccine.

3. The method of claim 1, wherein the IL-1 or IL-1 inducer is administered within 96 hours before or after the administration of the vaccine.

4. The method of claim 1, wherein the vaccine further comprises bacterins, toxoids, inactivated virus particles, modified live viral particles, other immunogenic components of pathogens, recombinant or synthesized subunits of the bacterins, toxoids, inactivated virus particles, modified live viral particles, or other immunogenic components of pathogens, or a combination of recombinant and synthesized subunits thereof.

5. The method of claim 1, wherein the IL-1 or IL-1 inducer, or the vaccine components, or both, are recombinantly produced.

6. The method of claim 5, wherein the recombinant IL-1 or IL-1 inducer is chemically or molecularly coupled to the vaccine or to a recombinant protein subunit in the vaccine.

7. The method of claim 1, wherein the IL-1 or IL-1 inducer is chemically or molecularly coupled to the vaccine or to a protein subunit in the vaccine.

8. The method of claim 1, wherein the IL-1 or IL-1 inducer is animal-cell derived.

9. The method of claim 1, wherein the mammal is bovine.

10. The method of claim 1, wherein the mammal is porcine.

11. A method of reducing or inhibiting antigenic interference associated with a vaccine comprising antigens from more than one pathogen in a mammal, comprising administering in conjunction with the vaccine an interleukin inducer, wherein the interleukin inducer is administered in a pharmaceutically acceptable vehicle.

12. A method of reversing or preventing antigenic interference in a mammal, wherein the antigenic interference is associated with a vaccine comprising antigens from more than one pathogen, said method comprising: administering in conjunction with the vaccine IL-1 or an IL-1 inducer or a combination thereof in a pharmaceutically acceptable vehicle.

13. The method of claim 12, wherein the IL-1 or IL-1 inducer is administered concurrently with the vaccine.

14. The method of claim 12, wherein the (interleukin) IL-1 or IL-1 inducer is administered within 96 hours before or after the administration of the vaccine.

15. The method of claim 12, wherein the vaccine further comprises bacterins, toxoids, inactivated virus particles, modified live viral particles, other immunogenic components of pathogens, recombinant or synthesized subunits of the bacterins, toxoids, inactivated virus particles, modified live viral particles, or other immunogenic components of pathogens, or a combination of recombinant and synthesized subunits thereof.

16. The method of claim 12, wherein the IL-1 or IL-1 inducer, or the vaccine components, or both, are recombinantly produced.

17. The method of claim 12, wherein the IL-1 or IL-1 inducer is chemically or molecularly coupled to the vaccine or to a protein subunit in the vaccine.

18. The method of claim 12, wherein the IL-1 or IL-1 inducer is animal-cell derived.

19. The method of claim 12, wherein the mammal is bovine.

20. The method of claim 12, wherein the mammal is porcine.

* * * * *